United States Patent [19]
Ozawa et al.

[11] Patent Number: 5,116,481
[45] Date of Patent: May 26, 1992

[54] ANION-SELECTIVE, SENSITIVE FILM, ELECTRODE CONTAINING THE SAME AND THE USE THEREOF

[75] Inventors: Satoshi Ozawa; Naoto Oki, both of Hitachi; Yasuhisa Shibata, Ibaraki; Hiroyuki Miyagi, Kokubunji, all of Japan

[73] Assignee: Hitachi, Ltd., Tokyo, Japan

[21] Appl. No.: 504,605

[22] Filed: Apr. 5, 1990

[30] Foreign Application Priority Data

Apr. 7, 1989 [JP] Japan .................................. 1-088906
Apr. 13, 1989 [JP] Japan .................................. 1-094172
Jul. 20, 1989 [JP] Japan .................................. 1-188201

[51] Int. Cl.⁵ .......................................... G01N 27/46
[52] U.S. Cl. ................................. 204/290 R; 204/416; 204/418; 252/62.3 Q; 252/500; 357/8; 422/82.03; 564/291; 568/9; 521/25
[58] Field of Search ............... 204/283, 284, 290 R, 204/291, 418, 416; 357/8; 422/82.03; 252/62.3 Q, 500; 564/291; 568/9; 521/25

[56] References Cited
U.S. PATENT DOCUMENTS 4,349,426 9/1982 Sugahara et al. .................. 204/418
4,670,127 6/1987 Ritter et al. ........................ 204/418
4,936,975 6/1990 Shibata et al. ..................... 204/416

FOREIGN PATENT DOCUMENTS 0842546 6/1981 U.S.S.R. ............................ 204/418

Primary Examiner—John Niebling
Assistant Examiner—Kathryn Gorgos
Attorney, Agent, or Firm—Fay, Sharpe, Beall, Fagan, Minnich & McKee

[57] ABSTRACT

An anion-selective electrode of the present invention comprises, as anion sensitive substance, a tetraalkyl type, quaternary phosphonium salt having four alkyl radicals, each having 8 to 24 carbon atoms; a combination of a tetraalkyl onium salt having four alkyl radicals each having 10 to 24 carbon atoms, and an onium salt having one alkyl radical with 1 to 20 carbon atoms and three alkyl radicals with the proviso that the number of carbon atoms contained in the three alkyl radicals each is larger than that contained in the one alkyl radical; or a tetraalkyl type, quaternary onium salt having an asymmetrical molecular structure. The anion-selective electrode has good properties including selectivity and measurement accuracy. An anion-selective, field effect transistor or a chemical analysis apparatus, provided with the anion-selective sensitive substance, is suitable for measuring an anion concentration with a high accuracy.

30 Claims, 10 Drawing Sheets

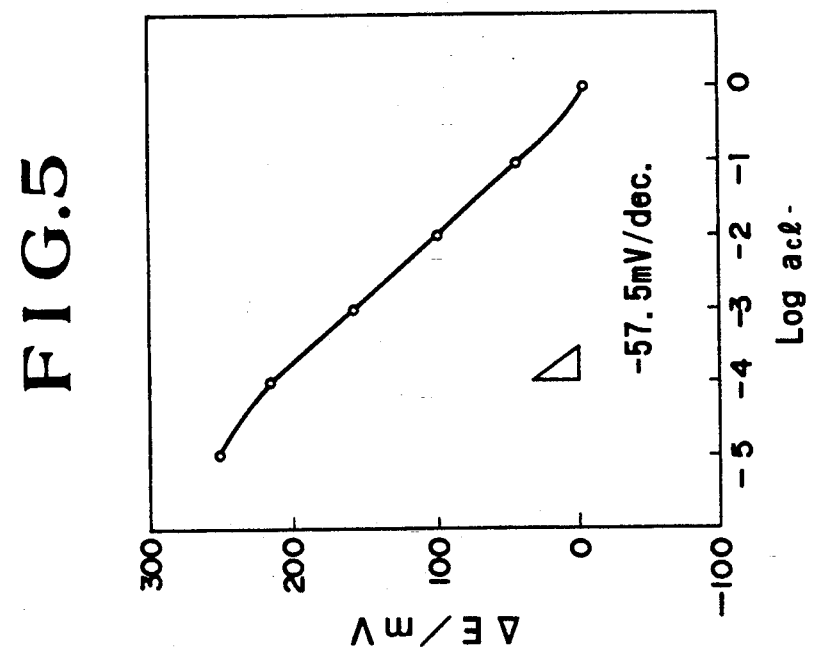
FIG.4
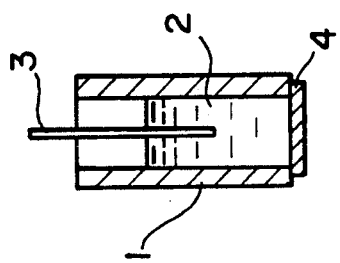
FIG.3
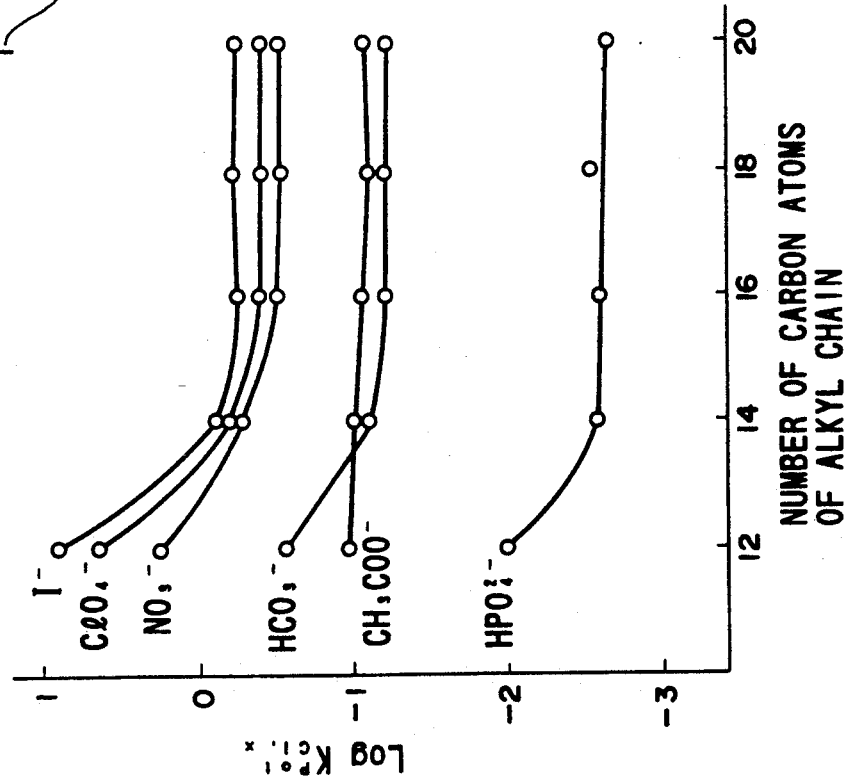

ANION-SELECTIVE, SENSITIVE FILM, ELECTRODE CONTAINING THE SAME AND THE USE THEREOF

BACKGROUND OF THE INVENTION

1. Field of the Invention

The present invention relates to an anion-selective, sensitive film containing an anion sensitive substance supported on a polymeric film, which is suitable for measuring inorganic anions, particularly chloride ions contained in body fluids, and to an anion-selective electrode using such a sensitive film. The invention also relates to an anion-selective field effect transistor, a biochemical analysis apparatus provided with such a transistor, and to a method of measuring anion concentration by employing such an anion-selective electrode or transistor.

2. Related Art Statement

It is known to use a solid film type electrode comprising silver chloride and silver sulfide as an anion-selective electrode for measuring anions contained in body fluids. It is also known to use a film type electrode comprising an ion exchanger material as sensitive film supported on a polymeric film such as polyvinyl chloride film. The former solid film type electrode has a drawback that its performance is rather low due to a large adverse effect of sulfide ions or halide ions such as bromide ions. On the other hand, the latter electrode has a short-coming that there might be an error of measurement due to adverse influences of lipophilic ions which are apt to deposit on the sensitive film.

Therefore, efforts have been made for an improvement of ion-selectivity of an electrode having a high polymer film type support. For instance, Japanese Patent Application Kokai (Laid-open) No. 56-63246 proposes to use a tetraalkyl ammonium chloride, which is an example of quaternary ammonium salts, as a sensitive substance, and also to use a straight chain alcohol as plasticizer.

Japanese Patent Application Kokai (Laid-open) No. 59-137851 discloses the use of a dimethyl dioctadecyl ammonium salt for an improvement of the selectivity for chloride ions and for reducing an adverse influence of lipophilic ions in the measurement of the aimed ions, particularly chloride ions.

In Mikrochimica Act (Wien), 1984 III, 1–16 (1984), it is mentioned that tetradodecyl ammonium salts, which belong to the class of tetraalkyl type, ammonium salts, have an improved selectivity for hydrophilic hydrogen carbonate ions.

However, it is noted that known chloride ion-selective electrodes, which contain the above-mentioned known sensitive substances, have a rather low selectivity for chloride ion over lipophilic ions but also low selectivity for chloride ion over hydrophilic ions. Thus, up to now, it has been difficult to improve not only the selectivity for lipophilic ions but also the selectivity for hydrophilic ions where use was made of the known sensitive substances. For the reasons mentioned above, there have occurred a number of problems about the characteristic properties of electrodes and the measurement accuracy when a measurement of a sample such as blood serum is made by employing any of the known electrodes.

Furthermore, an anion-selective electrode according to the prior art does not have a long effective time, so that the measurement accuracy would decrease after a relatively short period of time when the electrode is used for the measurement of a large number of controlled blood serum samples.

SUMMARY OF THE INVENTION

It is, therefore, an object of the invention to provide an anion-selective sensitive film and an electrode employing said film having good properties including selectivity and measurement accuracy and also having a stability for a long period of time.

It is another object of the invention to provide an anion-selective, field effect transistor which has a high accuracy when used in the measurement of practical samples.

It is still another object of the invention to provide an apparatus for the chemical analysis which has a high accuracy when used in the measurement of practical samples.

It is still another object of the invention to provide a process for the measuring of anion concentrations which has a high accuracy when used in the measurement of practical samples.

According to the first aspect of the invention, there is provided an anion-selective, sensitive film which contains an anion sensitive substance supported on a polymeric film containing a high polymer material and a plasticizer, wherein said anion sensitive substance is selected from the class consisting of: (A) a tetraalkyl type, quaternary phosphonium salt having four alkyl radicals each having 8 to 24 carbon atoms;

a compound having the formula:

wherein A represents a nitrogen or phosphorus atom, $X^-$ represents an anion, and $R_1$, $R_2$, $R_3$ and $R_4$ represent normal- or iso-alkyl radicals each containing the same number ($n_1$) of carbon atoms, wherein $n_1$ is an integer of 10 to 24, and a compound of the formula (1) wherein $R_1$ represents a normal- or iso-alkyl radical, the number ($n_2$) of carbon atoms contained in the alkyl radical being 1 to 20, and $R_2$, $R_3$ and $R_4$ represent normal- or iso-alkyl radicals each having the same number ($n_3$) of carbon atoms, with the proviso that $(n_2+1) \leq n_3 \leq 24$; and (C) a quaternary ammonium or phosphonium salt of the formula (1) wherein $R_1$, $R_2$ and $R_3$ represent alkyl radicals each having 10 to 23 carbon atoms, with the proviso that $n_1 \leq n_2 \leq n_3$ wherein $n_1$, $n_2$ and $n_3$ each represents the number of carbon atoms contained in the alkyl radicals $R_1$, $R_2$, and $R_3$, respectively, and $R_4$ represents an alkyl radical with the proviso that $9 \leq n_4 \leq (n_1-1)$ wherein $n_4$ represents the number of carbon atoms contained in the alkyl radical $R_4$.

In the second aspect of the invention, there is provided a liquid film type, anion-selective electrode which comprises an anion-selective, sensitive film containing an anion sensitive substance supported on a high polymer material, wherein the anion-selective, sensitive film is one as defined above.

In the third aspect of the invention, there is provided a liquid film type, anion selective, field effect transistor, which comprises an anion-selective, sensitive film containing an anion sensitive substance supported on a high polymer material, wherein the anion-selective, sensitive film is one as defined above.

In the fourth aspect of the invention, there is provided a chemical analysis apparatus for measuring an anion concentration which comprises an anion-selective electrode or an anion-selective, field effect transistor provided with an anion-selective, sensitive film containing an anion sensitive substance supported on a high polymer material, wherein the anion-selective, sensitive film is one as defined above.

In the fifth aspect of the invention, there is provided a method for measuring an anion concentration of body fluid which comprises effecting an anion concentration measuring operation by employing an anion-selective electrode or an anion-selective, field effect transistor provided with an anion-selective, sensitive film containing an anion sensitive substance supported on a high polymer material, wherein the anion-selective, sensitive film is one as defined above.

BRIEF DESCRIPTION OF DRAWINGS

FIG. 3 is a diagram illustrating relationships in tetraalkyl type, phophonium salts according to the embodiments of the invention between anion selectivity for various species of anions, and the number of carbon atoms contained in the alkyl radicals.

FIG. 4 is a longitudinal sectional view of a liquid film type, chloride ion-selective electrode according to an embodiment of the invention.

FIG. 5 is a diagram illustrating a calibration curve of electrodes employed in Example 1 according to the invention.

DETAILED DESCRIPTION OF THE INVENTION

Figure 1:
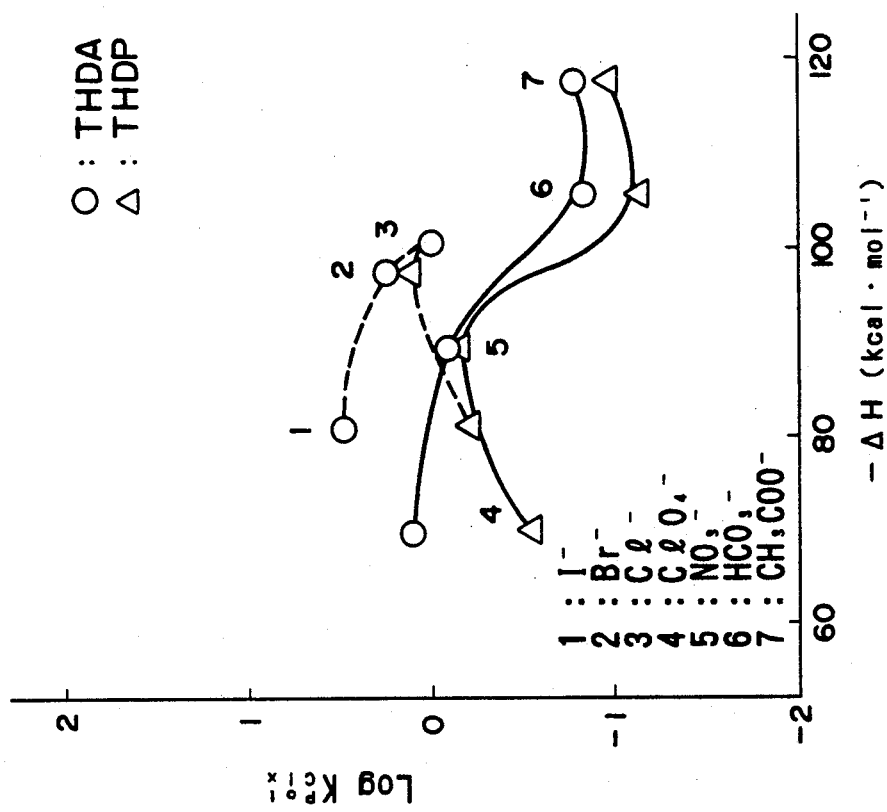
FIG. 1 is a diagram illustrating anion-selectivity of electrodes according to an embodiment of the invention, which contain trimethyl tridodecyl ammonium chloride (MTDA) or methyl tridodecyl phosphonium chloride (MTDP) as ligand, for various species of anions.

An anion-selective sensitive film which is employed in an anion-selective electrode based on a polymer support film is generally composed of an a ion sensitive substance, a plasticizer and a high polymer material as matrix material.

According to the invention, use is made of an anion sensitive substance selected from the class selected from consisting of:

(A) a tetraalkyl type, quaternary phosphonium salt having four alkyl radicals each having 8 to 24 carbon atoms;

(B) a combination of:

a compound having the formula:

wherein A represents a nitrogen or phosphorus atom, $X^-$ represents an anion, and $R_1$, $R_2$, $R_3$ and $R_4$ represent normal- or iso-alkyl radicals each containing the same number ($n_1$) of carbon atoms wherein $n_1$ is an integer of 10 to 24, and a compound of the formula (1) wherein $R_1$ represents a normal- or iso-alkyl radical, the number ($n_2$) of carbon atoms contained in the alkyl radical being 1 to 20, and $R_2$, $R_3$ and $R_4$ represent normal- or iso-alkyl radicals each having the same number ($n_3$) of carbon atoms, with the proviso that $(n_2+1) \leq n_3 \leq 24$; and (C) a quaternary ammonium or phosphonium salt of the formula (1) wherein $R_1$, $R_2$, and $R_3$ represent alkyl radicals, each having 10 to 24 carbon atoms, with the proviso that $n_1 \leq n_2 \leq n_3$ wherein $n_1$, $n_2$ and $n_3$ each represent the number of carbon atoms contained in the alkyl radicals $R_1$, $R_2$, and $R_3$, respectively, and $R_4$ represents an alkyl radical with the proviso that $9 \leq n_4 \leq (n_1-1)$, wherein $n_4$ represents the number of carbon atoms contained in the alkyl radical $R_4$.

An explanation will be made about the three kinds of the anion sensitive substances according to the invention.

(A) A detailed description is given below for the use of tetraalkyl type, quaternary phosphonium salts having four alkyl radicals with 8 to 24 carbon atoms as anion sensitive substances.

Generally, the anion-selectivity sequence of anion exchanger substances follows the Hofmeister Lyotropic series. In this series, it is observed that an anion will tend to occupy a higher position if said anion shows a smaller change in the Gibbs energy at the hydration of said anion. The Hofmeister lyotropic series is as follows:

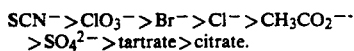

The tetraalkyl type, quaternary phosphonium salts having four alkyl radical with 8 to 24 carbon atoms, employed as sensitive substances according to the invention, are unique in that they partially deviate from the Hofmeister series, with respect to the selectivity for a few species of anions. Namely, they have a low selectivity for ions such as hydroxyl and fluoride ions which show a large change in the Gibbs energy at the hydration of said ions. On the other hand, the sensitive substances have a high selectivity for several other ions including chlorate, thiocyanate, iodide and nitrate ions, which exhibit a small change in the Gibbs energy at the hydration of said ions.

As mentioned above, the sensitive substances according to the invention show an improved selectivity for various ions except a few ions such as hydroxyl and fluoride ions. The concentration of hydroxyl and fluoride ions in body fluids is generally low so that these ions will not have a substantial adverse influence on the measurement operations according to the invention. Therefore, it can be said that a measurement of practical samples can be carried out with a high accuracy when use is made, for instance, of a liquid film type chloride ion-selective electrode provided with a sensitive substance according to the invention as mentioned above.

As the reason for the above mentioned change of the selectivity sequence, it is considered that the electrostatic interaction between the sensitive substances and the ions is rather low, so that the selectivity sequence is strongly influenced by other parameters.

Certain quarternery onium salts (such as quaternary ammonium salts and quaternary phosphonium salts), which have a positive charge, sometimes show a relatively low interactions with anions. This is true in case where the central heteroatoms (for example, nitrogen or phosphorus atoms) of the onium salts have a low positive charge density, or in case where the onium salts have large substituents such as alkyl radicals bonded to the central heteroatoms, so that the onium salts repel anions due to a steric hindrance formed there.

As an example of the former case, it may be mentioned for the onium salts that the positive charge density of a quaternary phosphonium salt containing a phosphorus atom as the central heteroatom is lower than that of a quaternary ammonium salt containing a nitrogen atom as the central heteroatom, if these two quaternary salts have the same four substituents. This is because the radius of the positively charged phosphorus atom is larger than that of the positively charged nitrogen atom.

In the latter case, it is noted for quaternary onium salts that the longer the alkyl radicals bonded to the central heteroatom or the larger the degree of branching of alkyl radicals is, the higher the degree of steric hindrance to the electrostatic interaction of the onium salts with anions. Furthermore, the positive charge density of central heteroatoms is lowered due to the I-effect, by which the degree of share of electrons from alkyl radicals to central heteroatoms is enhanced. In addition, as the lipophilicity of the sensitive substances is increased, they hardly dissolve out from the sensitive film, so that the liquid film type, chloride ion selective electrodes, prepared therefrom, have a long life, which is one of the advantages of the invention.

The sensitive substances according to the invention are the quaternary onium salts, wherein the central heteroatoms are phosphorus atoms, to which long alkyl radicals are bonded as substituents, so that the electrostatic interactions of the onium salts with anions are virtually low, and therefore, the onium salts have a high selectivity.

The invention will be further illustrated by way of embodiments with reference to the accompanying drawings.

FIG. 1 is a diagram showing the anion selectivity of electrodes containing methyl tridecyl ammonium chloride (MTDA) or methyl tridecyl phosphonium chloride (MTDP) as ligand. In the chloride ion-selective electrodes employing MTDA or MTDP, it is observed that the selectivity coefficients are nearly proportional to the enthalpy change at hydration. There is no substantial difference in selectivity coefficients between MTDA and MTDP.

Figure 2:
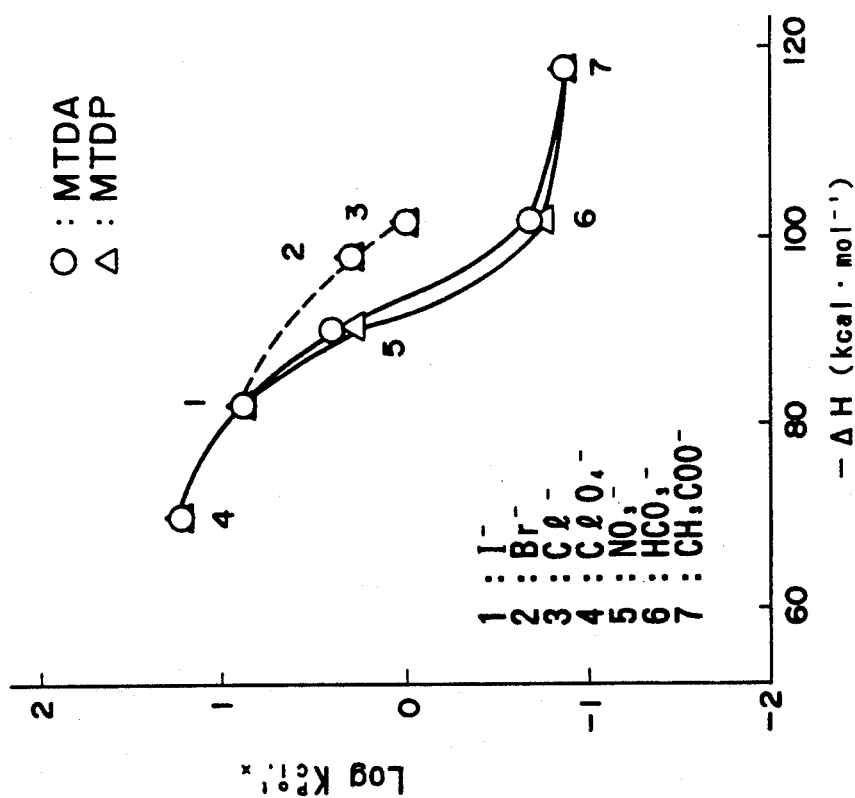
FIG. 2 is a diagram illustrating anion-selectivity of electrodes according to an embodiment of the invention, which contain tetrahexadecyl ammonium chloride (THDA) or tetrahexadecyl phosphonium chloride (THDP) as ligand, for various species of anions.

FIG. 2 shows the selectivity of chloride ion-selective electrodes provided with tetraalkyl type, onium salts having four long alkyl radicals. By comparing tetrahexadecyl ammonium chloride (THDA) with tetrahexadecyl phosphonium chloride (THDP), it will be seen that THDP has a high selectivity for iodide and perchlorate ions. From the above, it can be said that the selectivity of quaternary onium salts is not greatly enhanced by merely replacing the nitrogen atom as the central heteroatom by the phosphorus atom. On the other hand, it has been found that a particular kind of onium salts, namely, tetraalkyl type, quaternary phosphonium salts, having four long alkyl radicals, are chloride ion-selective sensitive substances with a good selectivity.

FIG. 3 is a diagram showing relationships between the selectivity of electrodes and the number of carbon atoms contained in the alkyl radical, with respect to the electrodes which contain as the sensitive substances tetraalkyl type, quaternary phosphonium salts having the same four alkyl radicals. From this diagram, it will be seen that the selectivity of an electrode, which contains as sensitive substance tetra-tetradecyl phosphonium chloride (TTDP) with four alkyl radicals each having 14 carbon atoms, is far higher than that of an electrode which contains tetradodecyl phosphonium chloride (TDDP) with four alkyl radicals each having 12 carbon atoms.

Also, it is observed that there is no significant difference in selectivity among electrodes which contain as the sensitive substances TTDP type salts having $C_{14-20}$ alkyl radicals and a molecular weight of 820 to 1200, including tetrahexadecyl phosphonium chloride (THDP), tetraoctadecyl phosphonium chloride (TODP) and tetraeicosyl phosphonium chloride (TEP). It is especially noted that several electrodes, wherein each alkyl radical has 16 to 20 carbon atoms, have almost the same selectivity. However, TEP contains the alkyl radicals each having 20 carbon atoms, so that said alkyl radicals are highly lipophilic, and therefore, the ionization of TEP is suppressed. A TEP film has a resistance of at least 1 giga-ohms and generates much noise. Tetradocosyl phosphonium chloride (TDP) contains $C_{22}$ alkyl radicals and has a film resistance of at least 10 giga-ohms, so that such a film lacks an acceptable responsiveness. It is therefore considered that the number of carbon atoms contained in each alkyl radical should preferably be between 14 and 20, in view of selectivity and film resistance.

FIG. 4 is a longitudinal sectional view showing the structure of a chloride ion-selective electrode according to the invention. In this electrode, an internal electrolyte 2 is stored in a cylindrical body 1, and an internal electrode (Ag/AgCl) 3 is dipped in the internal electrolyte 2, while a sensitive film 4 is applied to one end of the body 1. The internal electrolyte 2 may be a sodium chloride solution having a concentration of 10 mmol/l.

EXAMPLE 1

In Example 1, use was made of TTDP as the chloride ion sensitive substance. Fifteen percent by weight of the sensitive substance, 40% by weight of n-tetradecyl alcohol (n-TDA) as plasticizer, and 45% by weight of polyvinyl chloride (PVC) having a molecular weight of 65,000 as high polymer material were mixed and dissolved in tetrahydrofuran as casting solvent. Thereafter, the solvent was removed by evaporation to obtain a sensitive film. The film was cut into a disc form corresponding to the size of body 1 of FIG. 4, and then bonded to the end of body 1. By using the plasticizer, it is possible for the sensitive substance to freely migrate through the sensitive film. Although n-TDA was used in Example 1, use may also be advantageously made of other plasticizers, including linear or branched aliphatic alcohols having at least 10 carbon atoms.

It is also possible to use a combination of two aliphatic alcohols having 10 to 40 carbon atoms, with the proviso that the number of carbon atoms contained in one alcohol is different by 1 from that of the other alcohol or that the melting point of one alcohol is different by 13° C. or less from that of the other alcohol. For instance, a combination of n-tetradecyl alcohol and n-tridecyl alcohol may be used.

In view of responsiveness, selectivity and other properties of anion-selective electrodes, it is suitable to use 5-50% by weight of aliphatic alcohols having a low dielectric constant in a sensitive film.

Together with aliphatic alcohols having a low dielectric constant, use may be made of organic compounds having a high dielectric constant. Examples of organic compounds having a high dielectric constant are o-nitrophenyl octyl ether, nitrobenzene, and derivatives thereof, such as 0-, m- and p-nitrotoluenes, and acetophenone and derivatives thereof. The amount of these organic compounds in a sensitive film may be 3 to 20% by weight.

The amount of quaternary phosphonium salts dispersed into a sensible film is suitably 5 to 30% by weight, in view of responsiveness, selectivity and reduced film impedance.

Although Example 1 employs the polyvinyl chloride (PVC) as high polymer material for supporting the sensitive substance and the plasticizer, it is also possible to employ other high polymer materials, including polycarbonates, silicone rubbers, epoxy resins and the like.

When the content of high polymer materials in a sensitive film is below 25% by weight, then the mechanical strength of the sensitive film is very low owing to other components involved. On the other hand, if the content of polyvinyl chloride is more than 60% by weight, then the film impedance is very high so that it is difficult to obtain a stable electrode having good properties. It is, therefore, preferred to use high polymer materials in an amount of 25 to 60% by weight.

FIG. 5 is a diagram showing a calibration curve of the electrode according to Example 1. The curve in the diagram involves a straight line portion at an area corresponding to a chloride ion concentration range of $1 \times 10^{-4}$ to $1 \times 10^{-1}$ mol/l. The slope sensitivity was $-57.5$ mV/decade.

EXAMPLE 2

In Example 2, THDP was used as the chloride ion-sensitive substance. As in the case of Example 1, a sensitive film was prepared by employing 15% by weight of the sensitive substance, 40% by weight of n-TDA and 45% by weight of PVC. The sensitive film was applied to a cylindrical body to produce a chloride ion-selective electrode.

EXAMPLE 3

In Example 3, use was made of TODP as the chloride ion sensitive substance. A chloride ion-selective electrode was produced in a manner similar to that disclosed in Example 1.

EXAMPLE 4

In Example 4, TEP was employed as the chloride ion sensitive substance. A chloride ion selective electrode was produced in a manner similar to that shown in Example 1.

EXAMPLE 5

In Example 5, use was made, as the chloride ion sensitive substance, of tetra(2-methylpentadecyl)phosphonium chloride (TMPP) having the formula:

In a manner similar to that shown in Example 1, a chloride ion-selective electrode was prepared.

EXAMPLE 6

In Example 6, a chloride ion-selective electrode was produced in a manner similar to that shown in Example 1, by using as the chloride ion sensitive substance ditetradecyl dioctadecyl phosphonium chloride (DTDOP) of the formula:

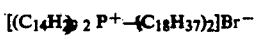

Figure 6:
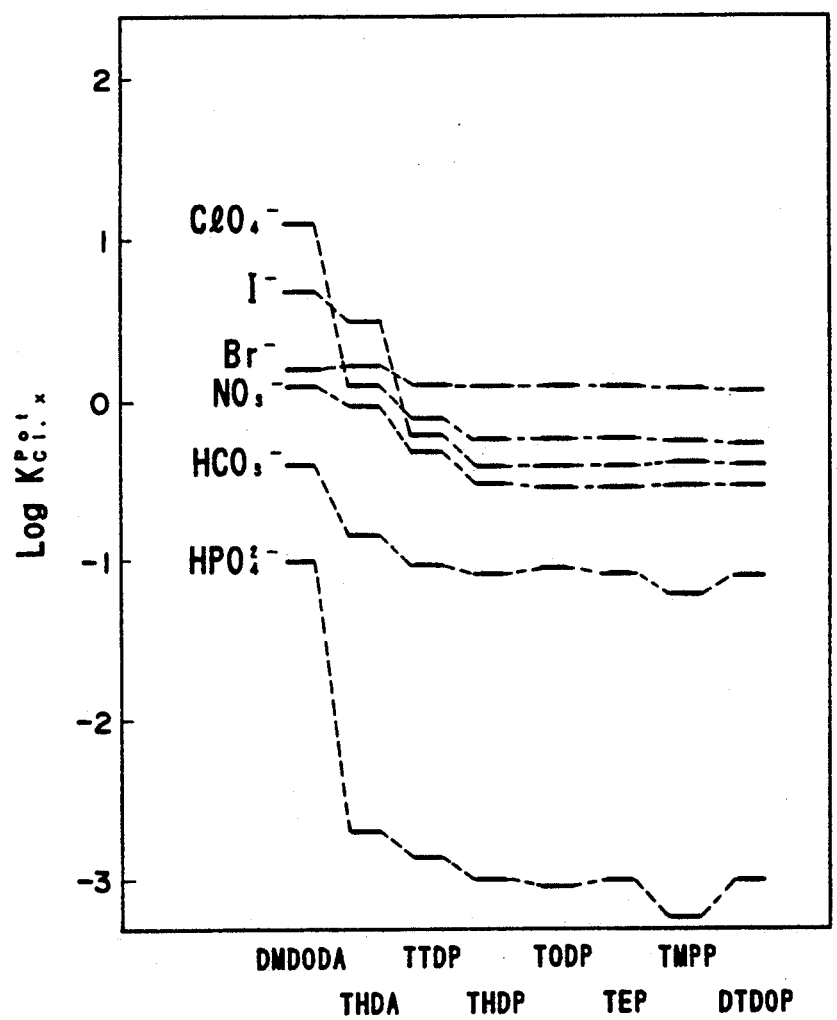
FIG. 6 is a diagram showing selectivity of electrodes employed in Examples 1 to 6 according to the invention for various species of anions.

FIG. 6 is a diagram showing selectivity of the chloride ion-selective electrodes of Examples 1 to 6 according to the invention, and the sensitivity of known chloride ion-selective electrodes. In the known electrodes, use was made of dimethyl dioctadecyl ammonium chloride (DMDODA) and tetrahexadecyl ammonium chloride (THDA) as sensitive substances.

The sensitive films according to Examples 1 to 6 each contained 15% by weight of the sensitive substance, 40% by weight of n-TDA and 45% by weight of PVC. In comparing the two known sensitive substances, namely, DMDODA and THDA, with the other, it is observed that the electrode containing THDA as sensitive substance has a better selectivity. The THDP, which is a sensitive substance employed in the invention, has four hexadecyl radicals, as in the case of the known THDA. It has been found that the substitution of nitrogen atom as the central heteroatom with a phosphorus atom results in an improvement of selectivity. As for the electrode, which contains TTDP as sensitive substance, it is noted that TTDP has four tetradecyl radicals each having 14 carbon atoms. Thus, the number of carbon atoms contained in each tetradecyl radical is smaller by 2 than that of a hexadecyl radical. Nevertheless, the selectivity of the electrode, which contains TTDP as sensitive substance, is better than that of known electrodes containing DMDODA or THDA. The selectivity of electrodes containing TODP, TEP, TMPP or DTDOP as sensitive substance is as high as that of electrode containing THDP. As TMPP has branched alkyl radicals, the selectivity of TMPP is better than that of THDP. The selectivity of electrodes according to the invention is far better than that of known electrodes, for chloride ion over anions including perchlorate and iodide ions.

Figure 7A:
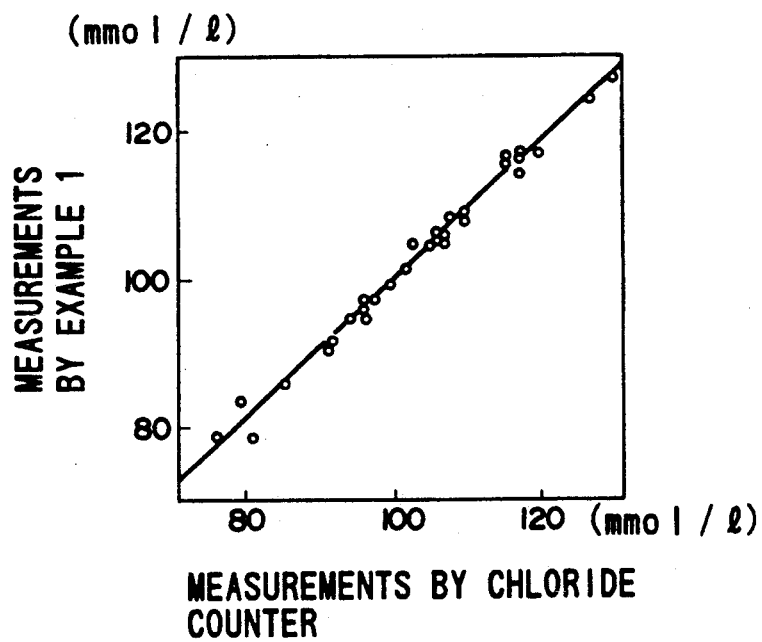
FIG. 7a is a diagram showing correlations between measurements by the electrode employed in Example 1 according to the invention, and those by a standard coulometry method with a chloride counter.
Figure 7B:
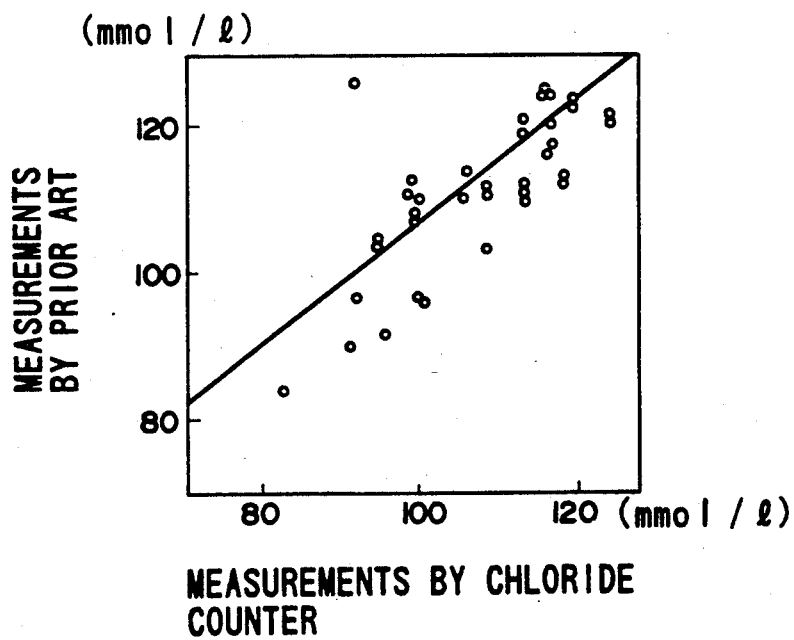
FIG. 7b is a diagram showing correlations between measurements by a known electrode, and those by a standard coulometry method with a chloride counter.
Figures 8, 9, 10:
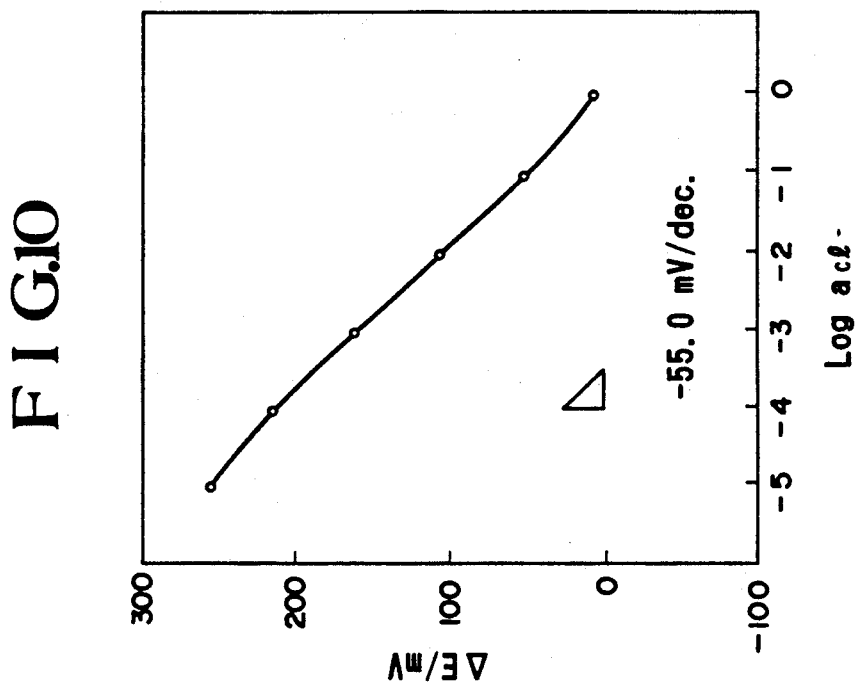
FIG. 8 is a diagram showing error distributions of electrodes relative to a chloride counter.
FIG. 9 is a longitudinal sectional view of a liquid film type chloride ion-selective, field effect transistor.
FIG. 10 is a diagram showing a calibration curve of a liquid film type, chloride ion selective, field effect transistor according to an embodiment of the invention.

By employing the six electrodes according to the invention shown in FIG. 6, an operation was carried out for measuring chloride ion concentrations of commercially available, controlled blood serum samples. The measured values thus obtained were compared with those obtained by a standard coulometry with a chloride counter. FIG. 7a is a diagram showing a correlation between measurements by an electrode containing THDP as sensitive substance and those by the standard method. FIG. 7b is similar to FIG. 7a, except that DMDODA was used instead of THDP. FIG. 8 is a diagram showing error distributions Syx of these electrodes. From the correlation data, it is observed that the six electrodes according to the invention can produce virtually correct results of measurement with less measurement errors.

EXAMPLE 7

In Example 7, use was made of a compound, which has been prepared by forming a covalent bond between a quaternary phosphonium salt and a high polymer chain. The compound has the formula:

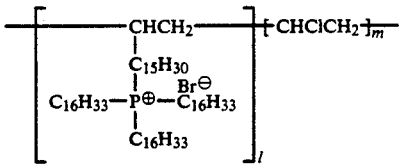

A sensitive film was prepared in a manner similar to that of Example 1, by employing 30% by weight of said compound, 40% by weight of o-nitrophenyl octyl ether and 30% by weight of PVC. The sensitive film was applied to a cylindrical body so as to form a chloride ion-selective electrode By chemically bonding the sensitive substance to PVC, any release of the sensitive substance was effectively suppressed.

EXAMPLE 8

In Example 8, use was made of a copolymer having the formula:

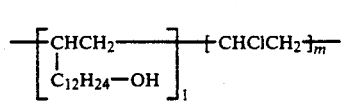

The copolymer contains a polymer chain having aliphatic alcohol plasticizer segments coupled via a covalent bond to the polymer chain.

A sensitive film was prepared in a manner similar to that of Example 1, by employing 85% by weight of the copolymer and 15% by weight of THDP. The sensitive film was applied to a cylindrical body to form a chloride ion-selective electrode.

As explained above, a sensitive substance or a plasticizer can be chemically bonded to PVC. The resulting modified PVC can be directly used in preparing a sensitive film.

By employing the chloride ion-selective electrodes of Examples 7 and 8, an operation was carried out for the measurement of chloride ion concentrations in commercially available, controlled blood serum samples. In addition, a correlation was made between the measurements by the electrodes of Examples 7 and 8, and those by a standard coulometry with a chloride counter. When the chloride ion-selective electrodes of Examples 7 and 8 were used, the values Syx were 1.6 and 1.5 mmol/l, respectively. Thus, the measurement accuracy of the chloride ion-selective electrodes according to the invention is far better than that of other electrodes containing known sensitive substances. Assuming that the effective life of an electrode may be represented by a period of time during which the electrode holds a slope sensitivity of at least $-30$ mV/decade, it can be said that the number of possible measurements of human serum samples by the chloride ion-selective electrodes of Examples 1 to 6 according to the invention is about 7,000 or more, whereas the number by the electrodes of Examples 7 and 8 according to the invention is about 10,000 or more. Thus, the electrodes of Examples 7 and 8 have a virtually improved effective life.

EXAMPLE 9

Example 9 relates to the use of a field effect transistor as liquid film type, chloride ion-selective electrode. FIG. 9 is a sectional view of a liquid film type, ion-selective, field effect transistor employed according to the invention. In FIG. 9, the transistor contains a drain 6, a source 7 and an oxide film 8 on a silicon substrate 5. A high polymer insulation film 9 and a sensitive film 10 are placed on the oxide film 8. The sensitive film was prepared in the manner shown below. Fifteen percent by weight of THDP as chloride ion sensitive substance, 40% by weight of n-TDA as plasticizer and 45% by weight of PVC were mixed and dissolved in 2 ml of tetrahydrofuran. The resulting solution was directly casted into the shape of a film on the oxide film 8, and dried in air.

FIG. 10 is a diagram showing a calibration curve of the chloride ion-selective, field effect transistor of Example 9 according to the invention.

By employing the field effect transistor according to the invention, an operation was carried out for the measurements of chloride ion concentrations in commercially available, controlled blood serum samples. A correlation was made between the measurements by the transistor, and those by a standard method with a chloride counter. The error distribution was 1.5 mmol/l, and the correlation coefficient was 0.993. From the observation of the period of time during which the slope sensitivity of at least $-30$ mV/decade was maintained, it has been found that the number of possible measurements of human blood serum samples by the transistor is about 100. Thus, the effective life of the transistor was rather short.

EXAMPLE 10

Figure 11:
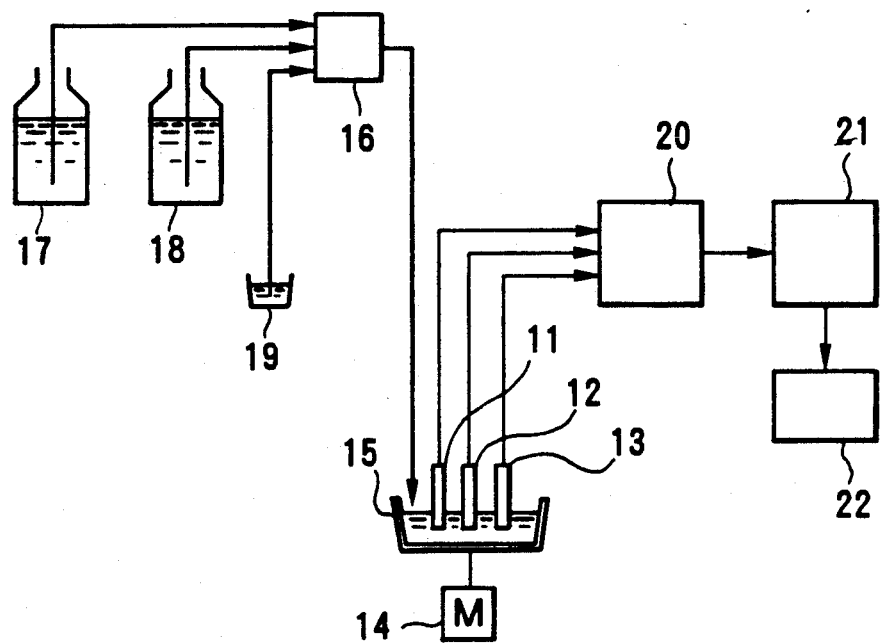
FIG. 11 is a schematic view of a biochemical analysis apparatus according to an embodiment of the invention.

Example 10 relates to a biochemical analysis apparatus provided with a liquid film type, chloride ion-selective electrode as a chemical sensor for chloride ions. FIG. 11 is a schematic view of a biochemical analysis apparatus of Example 10. In FIG. 11, the analysis apparatus has a chloride ion-selective electrode 11 which contains THDP as the sensitive substance. The apparatus also has a potassium ion-selective electrode 12 and a sodium ion-selective electrode 13. These three ion-selective electrodes are dipped in a measuring vessel 15, which is rotated by a motor 14. A correction is effected by using correction solutions 17 and 18 which are supplied through a switch valve 16. Then, a sample 19 is analyzed. The voltages measured are supplied to an amplifier 20, and then to a data collection unit 20, where the ion concentration values are calculated out, the results of which are sent to a display unit 22 for indicating the concentrations of chloride, potassium and sodium ions.

By employing the analytical apparatus mentioned above, an operation was effected for measurements of chloride ion concentrations of 50 human blood serum samples. A correlation was made between the chloride ion concentration measurements by using the analytical apparatus according to the invention, and those by a standard coulometry with a chloride counter. A good correlation was obtained. The error distribution Syx was 0.55 mmol/l, and the correlation coefficient was 0.998.

(B) As noted in the preceding paragraphs, it is also possible according to the invention to use, as an anion-selective substance, a combination of:
a compound (group 1 compound) of the formula:

(1)

wherein A represents a nitrogen or phosphorus atom, $X^-$ represents an anion, and $R_1$, $R_2$, $R_3$ and $R_4$ represent normal- or iso-alkyl radicals each containing the same number ($n_1$) of carbon atoms wherein $n_1$ is an integer of 10 to 24, and a compound of (group 2 compound) the formula (1) wherein $R_1$ represents a normal- or iso-alkyl radical, the number ($n_2$) of carbon atoms contained in the alkyl radical being 1 to 20, and $R_2$, $R_3$ and $R_4$ represent normal- or iso-alkyl radicals each having the same number ($n_3$) of carbon atoms, with the proviso that $(n_2+1) \leq n_3 \leq 24$. An explanation of the combination (B) of compounds will be made in the following paragraphs.

The quaternary onium salts of the group 1 compound has the formula (1), wherein $R_1$, $R_2$, $R_3$ and $R_4$ are normal- or iso-alkyl radicals each having the same number ($n_1$) of carbon atoms wherein $n_1$ is a number of 10 to 24. The compounds have four long alkyl radicals around the nitrogen atom, and therefore, the nitrogen atom is hardly attacked by large anions including hydrophilic hydrogenphosphate and hydrogencarbonate ions, and lipophilic hydrogenperchlorate ions. Accordingly, an anion-selective electrode, which contains a quaternary onium compound of the group 1 compound as the sensitive substance, is not adversely influenced by various large anions, and therefore has a high selectivity. However, the quaternary onium salts of the group 1 compound have a rather low ionization degree, and the molecular structure of the salts has a high symmetry. Accordingly, the salts have a rather low surface activity, so that the orientation degree of the salts is relatively low at an interface between oil phase and water phase on the surface of sensitive film. Therefore, if the quaternary onium salts of the group 1 compound are used alone in a measurement, then the ion exchange sites of the salts will be contaminated with a certain substance during the measurement, so that the selectivity of the salts will decrease.

On the other hand, in the case of the compounds of the group 2 compound, the ionization degree is relatively high, and the symmetry of the molecular structure is rather low. Accordingly, these compounds have a high surface activity. Also, the orientation degree of the compounds is relatively high at an interface between oil phase and water phase on the surface of the sensitive film.

Therefore, if a sensitive film is prepared by employing a compound of the group 1 compound together with a compound of the group 2 compound which has the properties supplementing the drawbacks of the former compound, then the resulting sensitive film will have the following good properties: the film provides effective ion exchange sites so as to enhance the responsiveness of the electrode; the slope sensitivity is high; the electrical resistance is low; and the good performance of the electrode can be maintained for a long period of time.

As mentioned above, it is possible to produce an electrode having a high selectivity and a long effective life, by mixing in a suitable proportion a compound of the group 1 compound having a high selectivity as the sensitive substance with a compound of the group 2 compound which provides effective ion exchange sites.

As the quaternary onium salts of the group 1 compound according to the invention, use may be made of tetraalkyl onium salts. Examples of such quaternary onium salts are tetraalkyl onium salts having four alkyl radicals each having 10 to 24 carbon atoms, such as tetradodecyl ammonium salts, tetracetyl ammonium salts, tetraoctadecyl ammonium salts and the like.

Examples of the quaternary onium salts of the group 2 compound are onium salts having one alkyl radical with 1 to 20 carbon atoms and three other alkyl radicals, wherein the number of carbon atoms contained in the three other alkyl radicals each is larger than that contained in the former radical, such as hexadecyltrioctadecyl ammonium salts, butyl trioctadecyl ammonium salts, methyl trioctadecyl ammonium salts ethyl trihexadecyl ammonium salts, methyl tritetradecyl ammonium salts and the like.

Next, a further explanation will be made by way of the Examples with reference to the accompanying drawings.

EXAMPLE 11

Example 11 relates to measurements of chloride ions. Use was made of tetraoctadecyl ammonium chloride as the quaternary ammonium salt of the group 1 compound. Hexadecyl trioctadecyl ammonium chloride was employed as the quaternary ammonium salt of the group 2 compound. A chloride ion-selective electrode was produced in the manner shown below.

Twelve percent by weight of the compound of the group 1 compound, 3% by weight of the compound of the group 2 compound, 25% by weight of n-tetradecyl alcohol, 5% by weight of n-tridecyl alcohol and 10% by weight of o-nitrophenyl octyl ether as plasticizer and 45% by weight of polyvinyl chloride as high polymer material are mixed and dissolved in tetrahydrofuran as solvent, optionally under heating. Then the solvent was removed so as to form an ion sensitive film. The film was cut into a disc form having an appropriate size. Then the film was applied to the end of the cylindrical body 1 shown in FIG. 4.

EXAMPLE 12

Tetraoctadecyl ammonium chloride was used as the quaternary ammonium salt of the group 1 compound and butyl trioctadecyl ammonium chloride was used as quaternary ammonium salt of the group 2 compound for the preparation of a chloride ion-selective electrode.

Twelve percent by weight of the compound of the group 1 compound, 3% by weight of the compound of the group 2 compound, 28% by weight of n-tetradecylalcohol, 2% by weight of n-tridecyl alcohol and 10% by weight of o-nitrophenyl octyl ether as plasticizer and 45% by weight of polyvinyl chloride as high polymer material were mixed and treated according to a method similar to that shown in Example 11 to form a sensitive film.

The compound of the group 2 compound, employed in Example 12, was one having a butyl radical having a relatively short chain length. When using a sensitive substance, such as the compound just mentioned above, which has a relatively high ionization tendency and surface activity, it is recommended that about 2% by weight of n-tridecyl alcohol should be added in order to obtain an electrode having high stability and good performance.

EXAMPLE 13

In Example 13, tetraoctadecyl ammonium chloride was used as the quaternary ammonium salt of the group 1 compound, and methyl trioctadecyl ammonium chloride was used as the quaternary ammonium salt of the group 2 compound for the production of a chloride ion-selective electrode.

Twelve percent by weight of the sensitive compound of the group 1 compound, 3% by weight of the sensitive compound of the group 2 compound, 30% by weight of n-tetradecyl alcohol and 10% by weight of o-nitrophenyl octyl ether as plasticizer and 45% by weight of polyvinyl chloride as high polymer material were mixed and treated in a manner similar to that of Example 11 to obtain a sensitive film.

The compound of the group 2 compound, employed in Example 13, was one having a methyl radical whose length was very short. Such a compound has relatively high ionization tendency and surface activity. In this case, it is possible to produce an electrode having good stability and properties, without any addition of n-tridecyl alcohol.

EXAMPLE 14

Tetraoctadecyl ammonium chloride was used as the quaternary ammonium salt of the group 1 compound, and ethyl trihexadecyl ammonium chloride was employed as the quaternary ammonium salt of the group 2 compound for the production of a chloride ion- sensitive electrode.

Twelve percent by weight of the sensitive compound of the group 1 compound, 3% by weight of the sensitive compound of the group 2 compound, 30% by weight of n-tetradecyl alcohol and 10% by weight of o-nitrophenyl octyl ether as plasticizer and 45% by weight of polyvinyl chloride as high polymer material were mixed and treated in a manner similar to that of Example 11 to prepare a sensitive film.

Example 14 is different from Example 13 in that Example 14 employs a quaternary ammonium salt of the group 2 compound wherein the longer alkyl radicals each have 16 carbon atoms, which are smaller than alkyl radicals having 18 carbon atoms shown in Example 13, and wherein the shorter alkyl radical has 2 carbon atoms, which is greater than that having 1 carbon atom shown in Example 13.

EXAMPLE 15

Example 15 relates to the measurement of nitrate ions.

Tetraoctadecyl ammonium nitrate was used as the quaternary ammonium salt of the group 1 compound, and methyl tritetradecyl ammonium nitrate was used as the quaternary ammonium salt of the group 2 compound for the preparation of a nitrate ion-selective electrode.

Five percent by weight of the sensitive compound of the group 1 compound, 10% by weight of the sensitive compound of the group 2 compound, 28% by weight of n-tetradecyl alcohol, 2% by weight of tridecyl alcohol and 10% by weight of o-nitrophenyl octyl ether as plasticizer and 45% by weight of polyvinyl chloride as high polymer material were mixed and treated in a manner similar to that of Example 11 to form a sensitive film.

In Example 15, a nitrate ion was used as the aimed ion $X^-$ in the formula (1). The amount of quaternary ammonium salt of the group 2 compound was larger than that of the quaternary ammonium salt of the group 1 compound. Therefore, an anion selective electrode which was highly selective to nitrate ions, was obtained.

EXAMPLE 16

Figure 12:
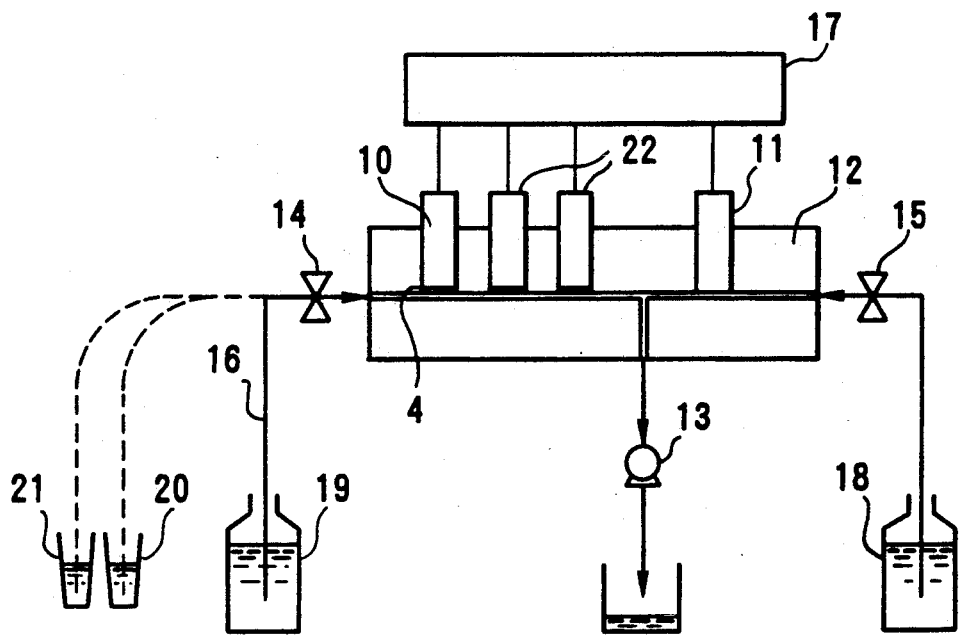
FIG. 12 is a schematic view of a biochemical analysis apparatus for the measurement of anion concentrations.

Example 16 is directed to a biochemical analysis apparatus as shown in FIG. 12. This apparatus comprises an anion-selective electrode 10 according to Example 11, and a reference electrode 11 kept in a flow-cell 12. Furthermore, the apparatus is provided with a solution supplier 13, valves 14 and 15, a sampling mechanism 16, a measurement/control unit 17, a solution 18 for the reference electrode, an internal standard solution 19, an external standard solution 20, a solution sample to be measured 21 and other electrodes 22.

The apparatus can be operated in a manner described below. With the aid of the solution supplier 13 and the valves 14 and 15, the solution 18 for reference electrode is supplied to the reference electrode 11 kept in the flow cell 12. The internal standard solution 19 is supplied as a solution sample to the anion-selective electrode 10. These two solutions are joined together in the flowcell 12 so as to form an electric path. Therefore, an electromotive force generates between the reference electrode 11 and the anion-selective electrode 10 depending on the activity of the aimed anion in the internal standard solution 19. The electromotive force in this case is measured. Next, the sampling mechanism 16 is operated so as to effect the electric measurements by employing the external standard solution 20 or the solution sample 21. A calibration curve is made on the basis of the observed values for the external standard solution 20, then the activity is calculated out on the basis of said calibration curve, and the data thus obtained are displayed or printed. The sensing and control operations are automatically carried out in the sensing/control unit 17 under a regulation by an operator.

Although Example 16 uses the chloride ion-selective electrode, it is also possible according to the invention to employ another anion-selective electrode. Furthermore, an anion-selective, field effect transistor can also be used in such a biochemical analysis apparatus.

REFERENCE EXAMPLE A

A chloride ion-selective electrode was prepared according to the teachings of Japanese Patent Application Kokai (Laid-open) No. 63-103935.

Fifteen percent by weight of tetraoctadecyl ammonium chloride as sensitive substance, 25% by weight of n-tetradecyl alcohol, 5% by weight of n-tridecyl alcohol and 10% by weight of o-nitrophenyl octyl ether as plasticizer, and 45% by weight of polyvinyl chloride as high polymer material were mixed for preparing a known electrode. Thus, the known electrode is different from that of the invention in that the known electrode lacks a quaternary ammonium salt of the group 2 compound.

Figure 13:
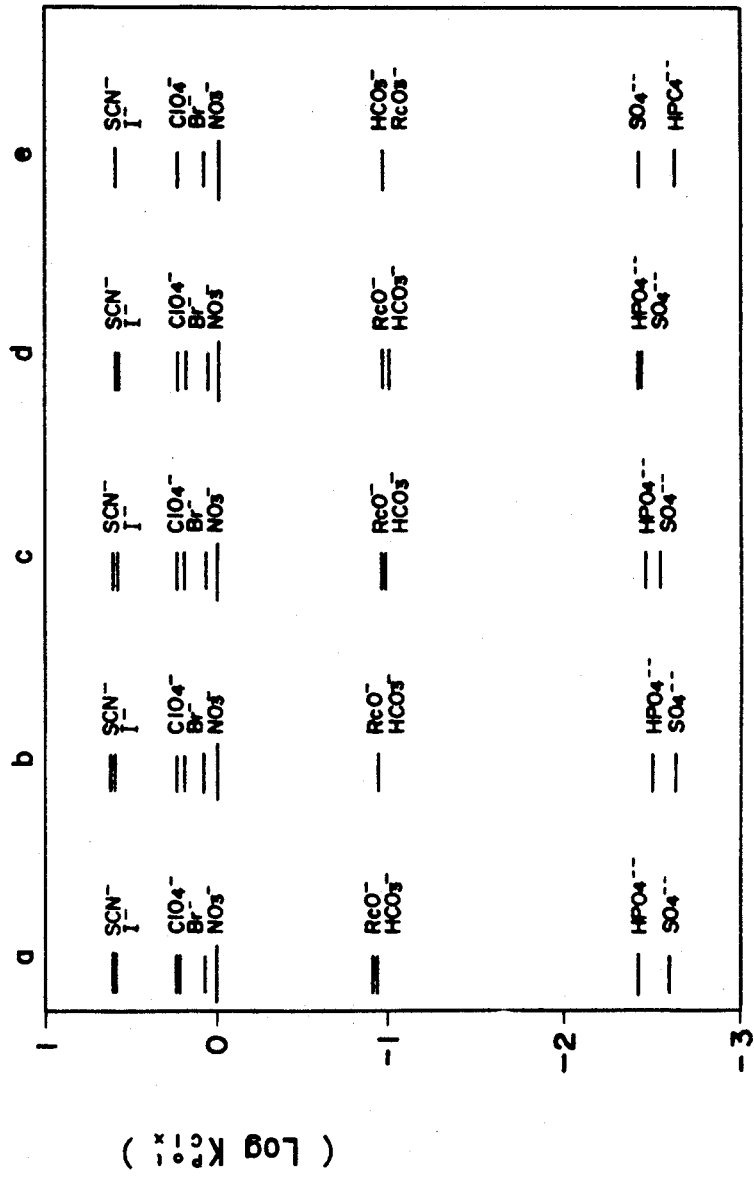
FIG. 13 is a diagram showing selectivity coefficients of chloride ion-selective electrodes according to the invention and chloride ion-selective electrodes according to the prior art for various species of anions.

FIG. 13 is a diagram showing selectivity coefficients of the chloride ion-selective electrodes of Examples 11 to 14 according to the invention, and the known electrode of Reference Example A for various species of anions. In FIG. 13, a shows the results of Reference Example A of the prior art, and b to e show the results of Examples 11 to 14, respectively, according to the invention. As is obvious from FIG. 13, the chloride ion-selectivity of the chloride ion-selective electrodes according to the invention is as high as that of the known electrode.

Figure 14:
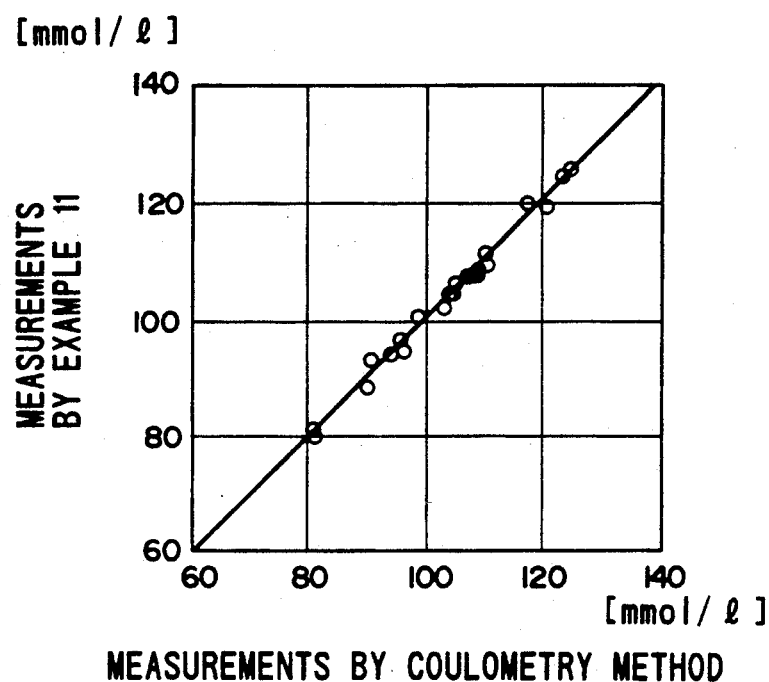
FIG. 14 is a diagram showing correlation between measurements of commercially available, controlled blood serum samples by the chloride ion-selective electrode of Example 11 according to, the invention, and those by a standard coulometry method.

FIG. 14 is a diagram showing a correlation between measurements of 23 species of commercially available controlled blood serum samples measured by the biochemical analysis apparatus of Example 16 according to the invention, and those by standard coulometry method with a chloride counter. It will be seen that a good correlation can be obtained with a higher accuracy and with a smaller error of measurement when the biochemical analytical apparatus is employed according to the invention.

Figure 15:
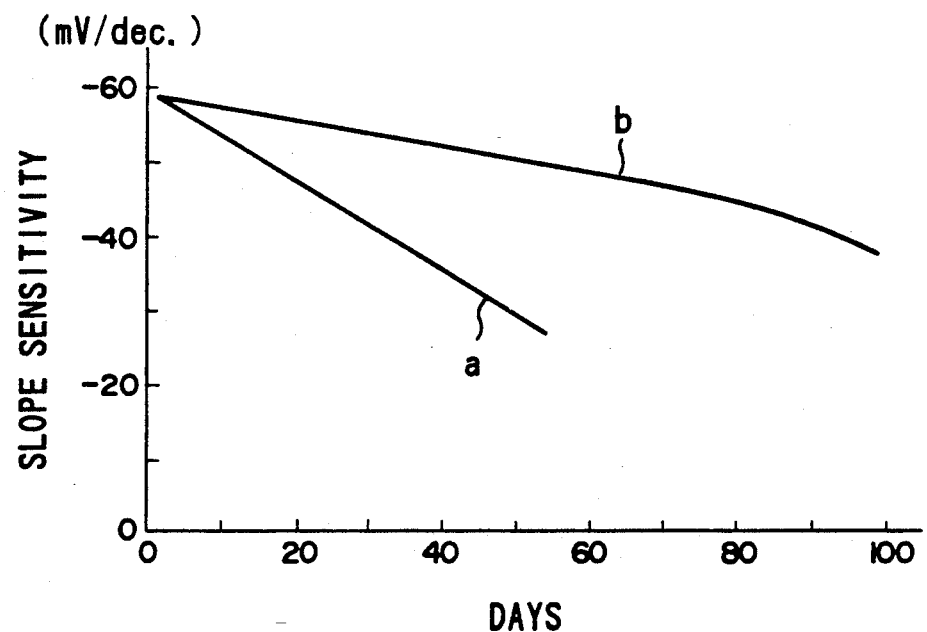
FIG. 15 is a diagram showing changes in slope sensitivity of chloride ion selective electrodes according to the invention and similar known electrodes, for a long period of time.

FIG. 15 is a diagram showing the relationship between days elapsed and changes in slope sensitivity of the chloride ion-selective electrode of Example 11 according to the invention and the known chloride ion-selective electrode of Reference Example A. When these electrodes were used in measurements of blood serum samples, it is observed that the slope sensitivity of the known chloride ion-selective electrode of Reference Example A (curve A) drops in a relatively short period of time, whereas the slope sensitivity of the electrode of Example 11 (curve b) according to the invention is maintained at a high value for a long period of time which is twice as long as that in the case of the known electrode. Similar results were also obtained when other known electrodes were used. The known electrodes contain as sensitive substance only a quaternary ammonium salt of the group 1 compound, which has low surface activity and insufficient ion exchange performance and responsiveness, so that the ion exchange performance of the known electrode will further drop after the electrode has been contacted with blood samples. On the other hand, the electrodes according to the invention contain quaternary salts of the group 1 compound together with quaternary ammonium salts of the group 2 compound, so that the ion exchange performance of the electrodes according to the invention can be kept for a long period of time, even after the electrodes have been contacted with blood samples. As mentioned above, the chloride ion-selective electrodes according to the invention have a far longer effective life as compared with known electrodes.

It is possible to produce anion-selective, field effect transistors and also to produce an analysis apparatus for the analysis of anions, as in the case of the anion sensitive substances (A) mentioned in the preceding paragraphs. Plasticizers and high polymer materials employed in the preparation of the sensitive film in this case may be the same as those described in the preceding paragraphs relating to the sensitive substances (A).

(C) The invention also includes the use of a quaternary ammonium or phosphonium salt of the formula (1) wherein $R_1$, $R_2$ and $R_3$ represent alkyl radicals each having 10 to 24 carbon atoms, with the proviso that $n_1 \leq n_2 \leq n_3$ wherein $n_1$, $n_2$ and $n_3$ represent the number of carbon atoms contained in the alkyl radicals $R_1$, $R_2$ and $R_3$, respectively, and $R_4$ represents an alkyl radical with the proviso that $9 \leq n_4 \leq (n_1 - 1)$ wherein $n_4$ represents the number of carbon atoms contained in the alkyl radical $R_4$.

An explanation will be made about the use of quaternary ammonium salts (C), which are ion exchangers, as anion sensitive substances. This may also apply to quaternary phosphonium salts (C).

Referring to the molecular structure of the quaternary salts and the interaction of the salts and ions, it is observed that, when large alkyl radicals are bonded to the nitrogen atom, large ions are hardly accessible to the nitrogen atom. Thus, the larger the radius of ions, the weaker the electrostatic interaction between the nitrogen atom and the ions. This has a relation with the ion selectivity of quaternary ammonium salts. Quaternary ammonium salts can be classified into the following four types: methyl trialkyl type, dimethyl dialkyl type, trimethyl alkyl type and tetraalkyl type. The highest steric hindrance effect due to large alkyl radicals may be obtained in the case of tetraalkyl ammonium salts.

As for relationships between the molecular structure and the solubility of quaternary ammonium salts, it is observed that the solubility will decrease with an increase of the number of carbon atoms contained in alkyl radicals bonded to the nitrogen atom, and with an increase of the degree of the symmetry of the molecule having four alkyl radicals.

In a sensitive film, a quaternary ammonium salt is dissolved in a plasticizer as solvent, and dispersed in a high polymer material.

The molecules of quaternary ammonium salts of the formula (1) have a symmetry lower than that of other tetraalkyl ammonium salts, wherein $R_1$ to $R_4$ represent alkyl radicals each having the same number of carbon atoms. Accordingly, the solubility of quaternary ammonium salts of the formula (1) is higher than that of the other tetraalkyl ammonium salts. Therefore, the quaternary ammonium salts of the formula (1) have a good steric hindrance effect an various species of ions, and also have an increased solubility in plasticizers, so that the electrodes containing the salts of the formula (1) have good performance and high stability for a long period of time.

As anion sensitive substances, it is possible to use quaternary onium salts having three alkyl radicals with 10 to 24 carbon atoms and one alkyl radical with 9 or more carbon atoms with the proviso that the number of carbon atoms contained in this radical is smaller by 1 than that of the former three alkyl radicals. Examples of the quaternary onium salts are hexadecyl trioctadecyl ammonium salts, tetradecyl trioctadecyl ammonium salts, dodecyl trihexadecyl ammonium salts, tetradecyl trihexadecyl ammonium salts and dodecyl tritetradecyl ammonium salts. As in the case of the above-mentioned quaternary ammonium salts, other quaternary onium salts having alkyl radicals similar to those described above also have ion exchange properties and therefore can be used according to the invention. The compounds concretely mentioned above are a mere illustration, and the invention is not limited to the use of these compounds.

Next, Examples will be shown with reference to the accompanying drawings.

EXAMPLE 17

A hexadodecyl trioctadecyl ammonium salt is used as the chloride ion sensitive substance.

Fifteen percent by weight of the above-mentioned chloride ion sensitive substance, 30% by weight of n-tetradecyl alcohol as plasticizer of group 1, 10% by weight of o-nitrophenyl octyl ether as plasticizer of group 2, and 45% by weight of polyvinyl chloride as high polymer material are mixed and dissolved in a fixed amount of tetrahydrofuran as solvent. Then the solvent is distilled off so as to form a sensitive film.

EXAMPLE 18

As the ion sensitive substance, use was made of hexadecyl trioctadecyl ammonium salt as in the case of Example 17. An n-tetradecyl alcohol was used as aliphatic alcohol of group 1, and n-tridecyl alcohol as aliphatic alcohol of group 2. A mixture of these two alcohols was employed as plasticizer of group 1. The amount of the alcohol of group 1 was 25% by weight, and the amount of the alcohol of group 2 was 5% by weight. The melting point of n-tridecyl alcohol is lower than that of n-tetradecyl alcohol. Accordingly, the use of n-tridecyl alcohol serves to increase the solubility of the sensitive substance, so that the resultant electrode has a reduced impedance and an enhanced responsiveness. It is preferred that the number of carbon atoms contained in an aliphatic alcohol of group 1 is different by 1 from that of an aliphatic alcohol of group 2, in view of selectivity for various species of ions and as well as stability of the resulting sensitive films. When two kinds of aliphatic alcohols are used, it is recommended in view of selectivity that the total amount of an aliphatic alcohol of group 1 and an aliphatic alcohol of group 2 in a sensitive film is between 5 and 40% by weight, and that the amount of the alcohol of group 2 in the film is between 1 and 20% by weight.

EXAMPLE 19

A hexadecyl trioctadecyl ammonium salt was used as ion sensitive substance. An n-tetradecyl alcohol was used as plasticizer of group 1, and 2-fluoro-2'-nitrodiphenyl ether having a dielectric constant of about 50 was employed as plasticizer of group 2. The amount of the above-mentioned substances in the resultant sensitive film was 15%, 30% and 10% by weight, respectively. The remaining component contained in the sensitive film was 45% by weight of polyvinyl chloride as matrix material. The dielectric constant of the organic compound used as plasticizer of group 2 is higher than the dielectric constant ($=24$) of o-nitrophenyl octyl ether. Accordingly, as compared with o-nitrophenyl octyl ether, the organic compound employed in Example 19 promotes more strongly the ionization of the ion sensitive substance contained in the sensitive film. Therefore, it may be also sufficient to use only one aliphatic alcohol of group 1.

EXAMPLE 20

Fifteen percent by weight of a dodecyl tritetradecyl ammonium salt was used as the ion sensitive substance. This compound has alkyl radicals shorter than those contained in the hexadecyl trioctadecyl ammonium salt employed in Examples 17, 18 and 19. Accordingly, this compound has a relatively high solubility. Therefore, use was made of only one aliphatic alcohol as alcohol of plasticizer of group 1. In other words, n-tridecyl alcohol, shown in Example 18, was not used. Even if only 30% by weight of n-tetradecyl alcohol was used, the resultant film had a reduced impedance. Other components and their contents in the sensitive film were the same as those of Example 17.

For the comparison of the invention with the prior art, there are given further two Reference Examples.

Reference Example B

Reference Example B relates to a known chloride ion-selective electrode disclosed in Japanese Patent Application Kokai (Laid-open) No. 56-63246.

The sensitive film contained 15% by weight of methyl tridecyl ammonium salt as the ion sensitive substance, 40% by weight of n-tetradecyl alcohol as plasticizer and 45% by weight of polyvinyl chloride as high polymer material.

Reference Example C

Reference Example C relates to a known chloride ion-selective electrode as disclosed in Japanese Patent Application Kokai (Laid-open) No. 59-137851. The sensitive film contained 15% by weight of a dimethyl dioctadecyl ammonium salt as ion sensitive substance, 30% by weight of n-tetradecyl alcohol and 10% by weight of o-nitrophenyl octyl ether as plasticizer, and 45% by weight of polyvinyl chloride as high polymer material.

Figure 16:
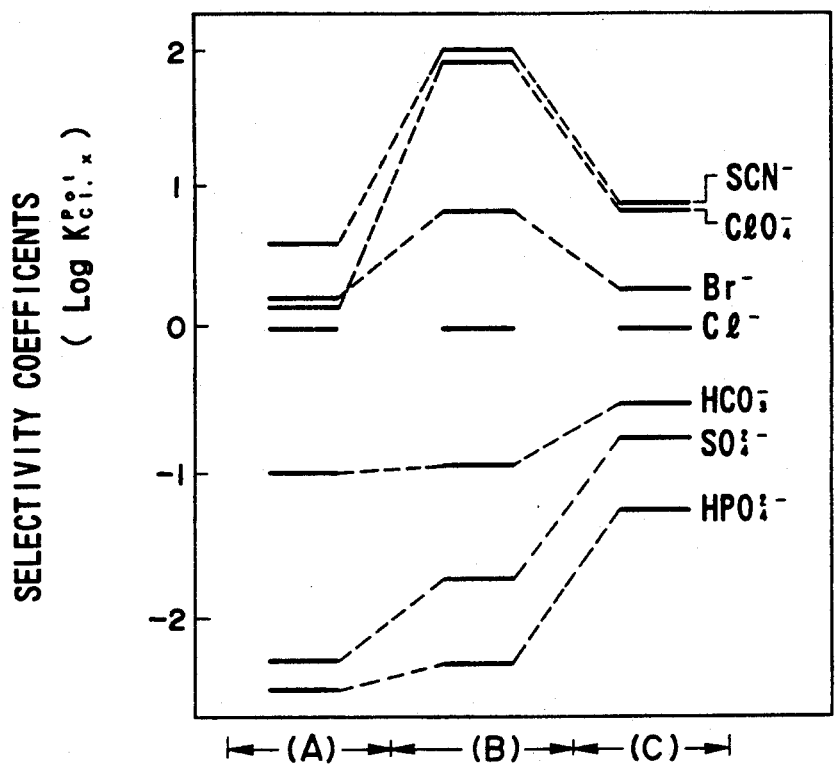
FIG. 16 is a diagram showing selectivity coefficients of chloride ion selective electrodes according to the embodiments of the invention and known electrodes.

FIG. 16 is a diagram showing selectivity coefficients of the following three chloride ion-selective electrodes: (A) Example 18 according to the invention, (B) Reference Example B according to the prior art and (C) Reference Example C according to the prior art. It will be seen from FIG. 16 that the electrode of Example 18 according to the invention is far better than the known electrodes of Reference Examples B and C, with respect to selectivity for chloride ion over lipophilic and hydrophilic ions.

Figure 17:
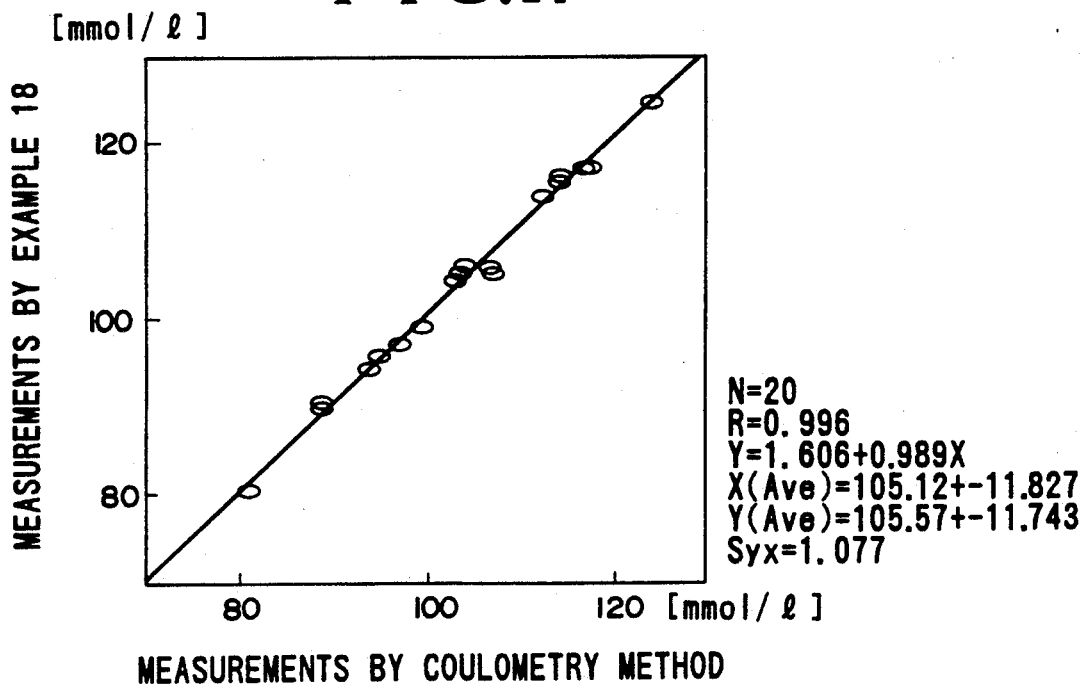
FIGS. 17 and 18 each is a diagram showing correlations of chloride between measurements of commercially available, controlled serum samples by chloride ion-selective electrodes according to the embodiments of the invention and known electrodes, and those by a standard practical method.
Figure 18:
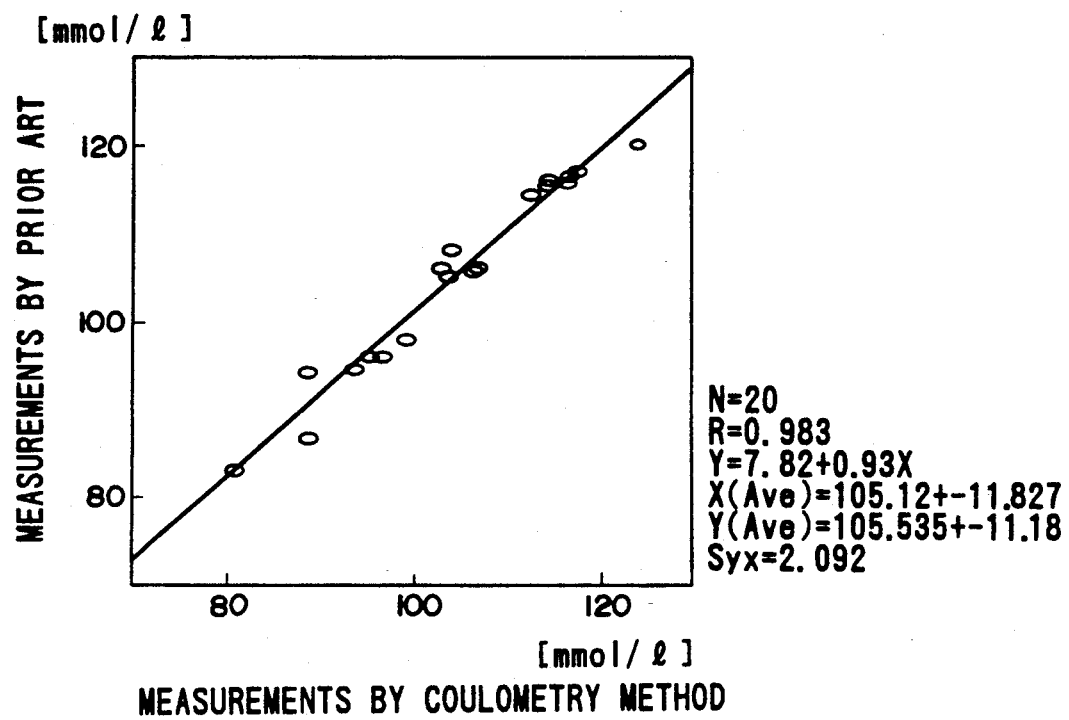

A study was conducted about a correlation of anion measurements of commercially available, controlled human blood serum samples by the use of anion-selective electrodes, and those by a coulometry as a standard method. The value or error distribution Syx were calculated out The values Syx represent the measurement accuracy. The smaller the values Syx are, the higher the measurement accuracy. As shown in FIGS. 17 and 18, the values Syx thus obtained are as follows: in Example 18, Syx=1.1 mmol/l, and in Reference Example C, Syx=2.1 mmol/l. In both Example 18 and Reference Example C, the slope sensitivity after the measurements of 100,000 blood serum samples was 50 to 52 mV/dec. Thus, there was no significant difference in slope sensitivity between Example 18 and Reference Example C.

However, in a correlation to a standard method of coulometry in measurements of commercially available, controlled blood serum samples, it was observed that Syx in Example 18 was 1.7 mmol/l and Syx in Reference Example C was 6.8 mmol/l. Thus, the known chloride ion-selective electrode of Reference Example C has a poor measurement accuracy, for the reason the selectivity of the known electrode is poorer than that of Example 18 according to the invention as shown in FIG. 17, and the selectivity of the known electrode undesirably changes. From the above, it can be said that measurements with a high accuracy can be conducted by using the chloride ion-selective electrode of Example 18 according to the invention.

Figure 19:
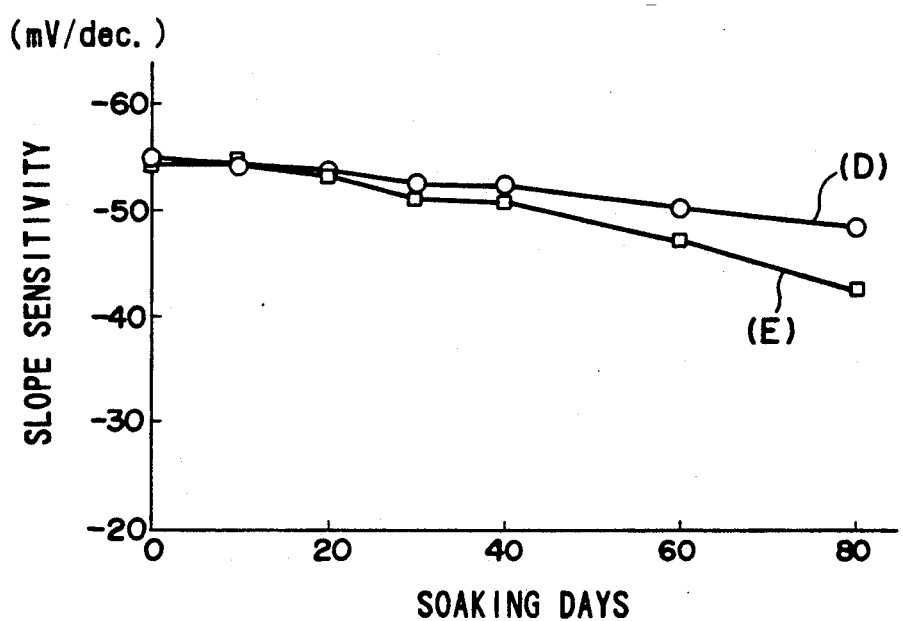
FIG. 19 is a diagram showing stability of chloride ion-selective electrodes according to the invention.

FIG. 19 is a diagram showing changes in slope sensitivity when the chloride ion-selective electrode of Example 18 according to the invention (curve D) and the known chloride ion-selective electrode of Reference Example B (curve E) are soaked in an aqueous solution. In comparing Example 18 with Reference Example B, there is no virtual difference in initial slope sensitivity between the two Examples. However, after a continued soaking, a difference in sensitivity is observed. Accordingly, it is believed that the stability of the electrode of Example 18 according to the invention is higher than that of Reference Example B according to the prior art.

As explained above, chloride ion-selective electrodes according to the invention have good properties including selectivity and accuracy, and also have good stability.

As in the case of the sensitive substances (A) mentioned in the preceding paragraphs, it is possible to produce an anion-selective, field effect transistor and also to produce an analysis apparatus for the analysis of anions. Plasticizers and high polymer substances employed in the preparation of the sensitive films in this case may be the same as those described in the preceding paragraphs relating to the sensitive substances (A).

What we claim is:

1. An anion-selective, sensitive film which contains an anion sensitive substance, a high polymer material and a plasticizer, wherein said anion sensitive substance comprises:
a combination of:
a first compound having the formula:

wherein A represents a nitrogen or phosphorus atom, $X^-$ represents an anion, and $R_1$, $R_2$, $R_3$ and $R_4$ represent normal- or iso-alkyl radicals each containing a number $n_1$ of carbon atoms wherein $n_1$ is an integer between 10 and 24 inclusive, and a second compound of the formula (1) wherein $R_1$ represents a normal-or iso-alkyl radical containing a number $n_2$ of carbon atoms between 1 and 20 inclusive, and $R_2$, $R_3$ and $R_4$ represent normal-or iso-alkyl radicals each having a number $n_3$ of carbon atoms, with the proviso that $(n_2+1) \leq n_3 \leq 24$.

2. An anion-selective, sensitive film as defined in claim 1, wherein the combination is a combination of:
the first compound being of the formula (1) wherein $R_1$, $R_2$, $R_3$ and $R_4$ represent normal- or iso-alkyl radicals each having a number $n_1$ of carbon atoms wherein $n_1$ is a number between 10 and 24 inclusive, and
the second compound being of the formula (1) wherein $R_1$ represents a normal- or iso-alkyl radical containing a number $n_2$ of carbon atoms between 1 and 9 inclusive, and $R_2$, $R_3$ and $R_4$ represent normal- or iso-alkyl radicals having a number $n_3$ of carbon atoms wherein $n_3$ represents a number between 10 and 24 inclusive.

3. An anion-selective, sensitive film as defined in claim 1, wherein the combination is a combination of:
the first compound being selected from the class consisting of tetradecyl ammonium salts, tetracetyl ammonium salts and tetraoctadecyl ammonium salts; and
the second compound being selected from the class consisting of hexadecyl trioctadecyl ammonium salts, butyl trioctadecyl ammonium salts, methyl trioctadecyl ammonium salts, ethyl trihexadecylammonium salts and methyl tritetradecyl ammonium salts.

4. An anion-selective, sensitive film as defined in claim 1, wherein the sensitive film contains a linear or branched aliphatic alcohol as the plasticizer dispersed therein.

5. An anion-selective, sensitive film as defined in claim 4, wherein the sensitive film contains an organic compound as plasticizer dispersed therein, and wherein the organic compound has a dielectric constant that is greater than that of the linear or branched aliphatic alcohol.

6. An anion-selective, sensitive film as claimed in claim 5, wherein the film contains 5 to 30% by weight of the anion sensitive substance, 5 to 50% by weight of the aliphatic alcohol, 3 to 20% by weight of the organic compound and 25 to 60% by weight of the high polymer material.

7. An anion-selective, sensitive film as defined in claim 4, wherein the aliphatic alcohol is one which has been chemically bonded to the high polymer material.

8. An anion-selective, sensitive film as defined in claim 1, wherein the high polymer material is polyvinyl chloride.

9. An anion-selective, sensitive film as defined in claim 1, wherein the anion sensitive substance is one which has been chemically bonded to the high polymer material.

10. An anion-selective, sensitive film as defined in claim 1, wherein the sensitive film is a chloride ion-selective, sensitive film.

11. A liquid film, anion-selective electrode which comprises an anion-selective, sensitive film containing an anion sensitive substance supported by a high polymer material, wherein the anion-selective, sensitive film is one as defined in claim 1.

12. A liquid film, anion-selective, field effect transistor which comprises an anion-selective, sensitive film containing an anion sensitive substance supported by a high polymer material, wherein the anion-selective, sensitive film is one as defined in claim 1.

13. A chemical analysis apparatus for measuring an anion concentration, comprising an anion-selective electrode provided with an anion-selective, sensitive film containing an anion sensitive substance supported by a high polymer material, wherein the anion-selective, sensitive film is one as defined in claim 1.

14. An anion-selective, sensitive film as claimed in claim 1, wherein the plasticizer is one which has been chemically bonded to the high polymer material.

15. A chemical analysis apparatus for measuring an anion concentration, comprising an anion-selective field-effect transistor provided with an anion-selective sensitive film containing an anion-sensitive substance supported by a high polymer material, wherein the anion-selective sensitive film is one as defined in claim 1.

16. An anion-selective, sensitive film as claimed in claim 1, wherein $n_2 1 = n_3$.

17. An anion-selective, sensitive film as claimed in claim 1, comprising 12 percent by weight of the first compound, 3 percent by weight of the second compound, 40 percent by weight of the plasticizer, and 45 percent by weight of the high polymer material.

18. An anion-selective, sensitive film as claimed in claim 17, comprising 25 percent by weight of n-tetradecyl alcohol, 5 percent by weight of n-tridecyl alcohol and 10 percent by weight of o-nitrophenyl octyl ether as plasticizer.

19. An anion-selective, sensitive film as claimed in claim 18, wherein the first compound is tetraoctadecyl ammonium chloride, and wherein the second compound is hexadecyl trioctadecyl ammonium chloride.

20. An anion-selective, sensitive film as claimed in claim 17, further comprising 28 percent by weight of n-tetradecyl alcohol, 2 percent by weight of n-tridecyl alcohol and 10 percent by weight of o-nitrophenyl octyl ether as plasticizer.

21. An anion-selective, sensitive film as claimed in claim 20, wherein the first compound is tetraoctadecyl ammonium chloride, and the second compound is butyl trioctadecyl ammonium chloride.

22. An anion-selective, sensitive film as claimed in claim 17, further comprising 30 percent by weight of n-tetradecyl alcohol and 10 percent by weight of o-nitrophenyl octyl ether as plasticizer.

23. An anion-selective, sensitive film as claimed in claim 22, wherein the first compound is tetraoctadecyl ammonium chloride and the second compound is methyl trioctadecyl ammonium chloride.

24. An anion-selective, sensitive film as claimed in claim 22, wherein the first compound is tetraoctadecyl ammonium chloride, and the second compound is ethyl trihexadecyl ammonium chloride.

25. An anion-selective, sensitive film as claimed in claim 1, comprising 5 percent by weight of the first compound, 10 percent by weight of the second compound, 40 percent by weight of the plasticizer, and 45 percent by weight of the high polymer material.

26. An anion-selective, sensitive film as claimed in claim 25, wherein the first compound is tetraoctadecyl ammonium nitrate, and the second compound is methyl tritetradecyl ammonium nitrate.

27. An anion-selective, sensitive film as claimed in claim 1, wherein $X^-$ is a chloride ion.

28. An anion-selective, sensitive film as claimed in claim 1, wherein $X^-$ is a potassium ion.

29. An anion-selective, sensitive film as claimed in claim 1, wherein $X^-$ is a sodium ion.

30. A biochemical analysis apparatus for measuring an anion concentration, comprising:
   an anion-selective electrode immersed in a first solution;
   a reference electrode immersed in a second solution;
   a flow cell, including means for combining said first and second solutions to form an electrically conductive path including the anion-selective electrode and the reference electrode;
   means for introducing a third solution into the flow cell;
   means for measuring an electromotive force generated between the reference electrode and the anion-selective electrode; and
   means for analyzing characteristics of the third solution based upon the electromotive force thus measured, wherein the anion-selective electrode includes an anion-selective sensitive film as defined in claim 1.

* * * * *